(12) United States Patent
Li

(10) Patent No.: US 8,123,402 B2
(45) Date of Patent: Feb. 28, 2012

(54) EAR THERMOMETER CRADLE AND ASSEMBLY THEREOF

(75) Inventor: Liang-Yi Li, Hsinchu (TW)

(73) Assignee: Actherm Inc., Hsinchu (TW)

( * ) Notice: Subject to any disclaimer, the term of this patent is extended or adjusted under 35 U.S.C. 154(b) by 216 days.

(21) Appl. No.: 12/713,979

(22) Filed: Feb. 26, 2010

(65) Prior Publication Data

US 2010/0232471 A1 Sep. 16, 2010

(30) Foreign Application Priority Data

Mar. 11, 2009 (WO) ................ PCT/CN2009/070743

(51) Int. Cl.
*G01K 1/08* (2006.01)

(52) U.S. Cl. ........ 374/158; 374/209; 374/120; 374/141; 374/208; 600/549

(58) Field of Classification Search .................. 374/120, 374/121, 141, 208, 209, 158; 600/549
See application file for complete search history.

(56) References Cited

U.S. PATENT DOCUMENTS

| 6,485,433 | B1 * | 11/2002 | Peng | 600/549 |
| 7,722,247 | B2 * | 5/2010 | Yerlikaya | 374/100 |
| 2004/0016766 | A1 | 1/2004 | Lin et al. | |

FOREIGN PATENT DOCUMENTS

WO WO9855841 (A2) 12/1998
* cited by examiner

*Primary Examiner* — Lisa Caputo
*Assistant Examiner* — Jamel Williams
(74) *Attorney, Agent, or Firm* — Ming Chow; Sinorica, LLC

(57) ABSTRACT

The present invention is an ear thermometer cradle and an ear thermometer assembly. The ear thermometer cradle comprises a hollow housing, a swivel arm, a probe cover container seat, a first elastic member disposed between the swivel arm and the hollow house. The ear thermometer cradle comprises a second elastic member between the container seat and the hollow housing. The hollow housing has an opening and a first blocking portion. The swivel arm includes a first pivot on one end thereof for pivotally connected with the hollow housing, a bearing portion on the other end thereof, and a second blocking portion between the first pivot and the bearing portion. The container seat includes a connective device, a second pivot on two lateral sides thereof for pivotally connected with the hollow housing, a third blocking portion and a forth blocking portion engaging with the first and the second blocking portion respectively.

20 Claims, 5 Drawing Sheets

EAR THERMOMETER CRADLE AND ASSEMBLY THEREOF

BACKGROUND OF THE INVENTION

1. Field of the Invention

The present invention is related to an ear thermometer cradle, and more particularly related to an ear thermometer cradle with an ear thermometer and a probe cover container.

2. Description of the Prior Art

The present ear thermometer in the market uses the electrical device to measure the infrared radiation generated by the human tympanum. The ear thermometer is easier to read and quicker to measure than the conventional mercury or ethanol thermometer. In order to prevent the cross infection between the patients caused by the reused medical equipments, those medical equipments are needed to disinfect. The conventional disinfection methods, such as the alcohol disinfection method, would damage the electrical elements of the ear thermometer. Therefore, a disposable probe cover is equipped with the sensing portion of the ear thermometer each time when the ear thermometer is used.

In order to maintain clean, the probe cover is stored in the probe cover container. However, the conventional probe cover container is separated from the ear thermometer, and it is wasting time to look for the probe cover container when people want to use the ear thermometer.

In order to overcome the inconvenience mentioned above, the conventional ear thermometer cradle assembly comprises a holder for accommodating a probe cover container, and the ear thermometer is able to install in the ear thermometer cradle after used. Therefore, when the user takes the ear thermometer from the ear thermometer cradle, the user can get the probe cover container at the same time, and the user will not waste time in finding the probe covers. However, it is still inconvenient for the user still needs to pull out the holder accommodating the probe cover container from the ear thermometer cradle.

SUMMARY OF THE INVENTION

In order to overcome the shortcomings mentioned above, the present invention discloses an ear thermometer cradle comprising a hollow housing, a swivel arm, a probe cover container, a first elastic member. The ear thermometer cradle may also comprise a second elastic member. The hollow housing includes an opening and a first blocking portion disposed therein. The swivel arm includes a first pivot on one end thereof for pivotally connected with the hollow housing, a bearing portion on the other end thereof, and a second blocking portion disposed between the first pivot and the bearing portion. The probe cover container seat includes a connective device therein, a second pivot on two lateral sides thereof for pivotally connected with the hollow housing, a third blocking portion and forth blocking portion engaging with the first blocking portion and the second blocking portion respectively. The first elastic member is disposed between the swivel arm and the hollow housing. The second elastic member is disposed between the probe cover container seat and the hollow housing.

The main object of the present invention is to provide an ear thermometer cradle with a probe cover container seat for storing the probe cover container conveniently.

Another object of the present invention is to provide an ear thermometer cradle with a probe cover container seat and the probe cover container can be took out by the relative motion of the swivel arm, the probe cover container, the first elastic member and the second elastic member.

The present invention further discloses an ear thermometer cradle assembly comprising an ear thermometer, a probe cover container and an ear thermometer cradle. The thermometer cradle comprises a hollow housing, a swivel arm, a probe cover container seat, a first elastic member. The ear thermometer cradle may also comprise a second elastic member. The hollow housing includes an opening and a first blocking portion disposed therein. The swivel arm includes a first pivot on one end thereof for pivotally connected with the hollow housing, a bearing portion on the other end thereof, and a second blocking portion disposed between the first pivot and the bearing portion. The probe cover container seat includes a connective device therein, a second pivot on two lateral sides for pivotally connected with the hollow housing, a third blocking portion and a forth blocking portion engaging with the first blocking portion and the second blocking portion respectively. The first elastic member is disposed between the swivel arm and the hollow housing. The second elastic member is disposed between the probe cover container seat and the hollow housing.

Another object of the present invention is to provide an ear thermometer assembly with a probe cover container seat for storing the probe cover container conveniently.

Another object of the present invention is to provide an ear thermometer assembly with a probe cover container seat and the probe cover container can be took out by the relative motion of the swivel arm, the probe cover container, the first elastic member and the second elastic member.

One another object of the present invention is to provide an ear thermometer assembly and the user can take out the ear thermometer by one hand.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

A detailed description of the present invention will be given below with reference to preferred embodiments thereof, so that a person skilled in the art can readily understand features and functions of the present invention after reviewing the contents disclosed herein. The present invention can also be implemented by or applied in other embodiments, where changes and modifications can be made to the disclosed details from a viewpoint different from that adopted in this specification without departing from the spirit of the present invention.

Figure 1A:
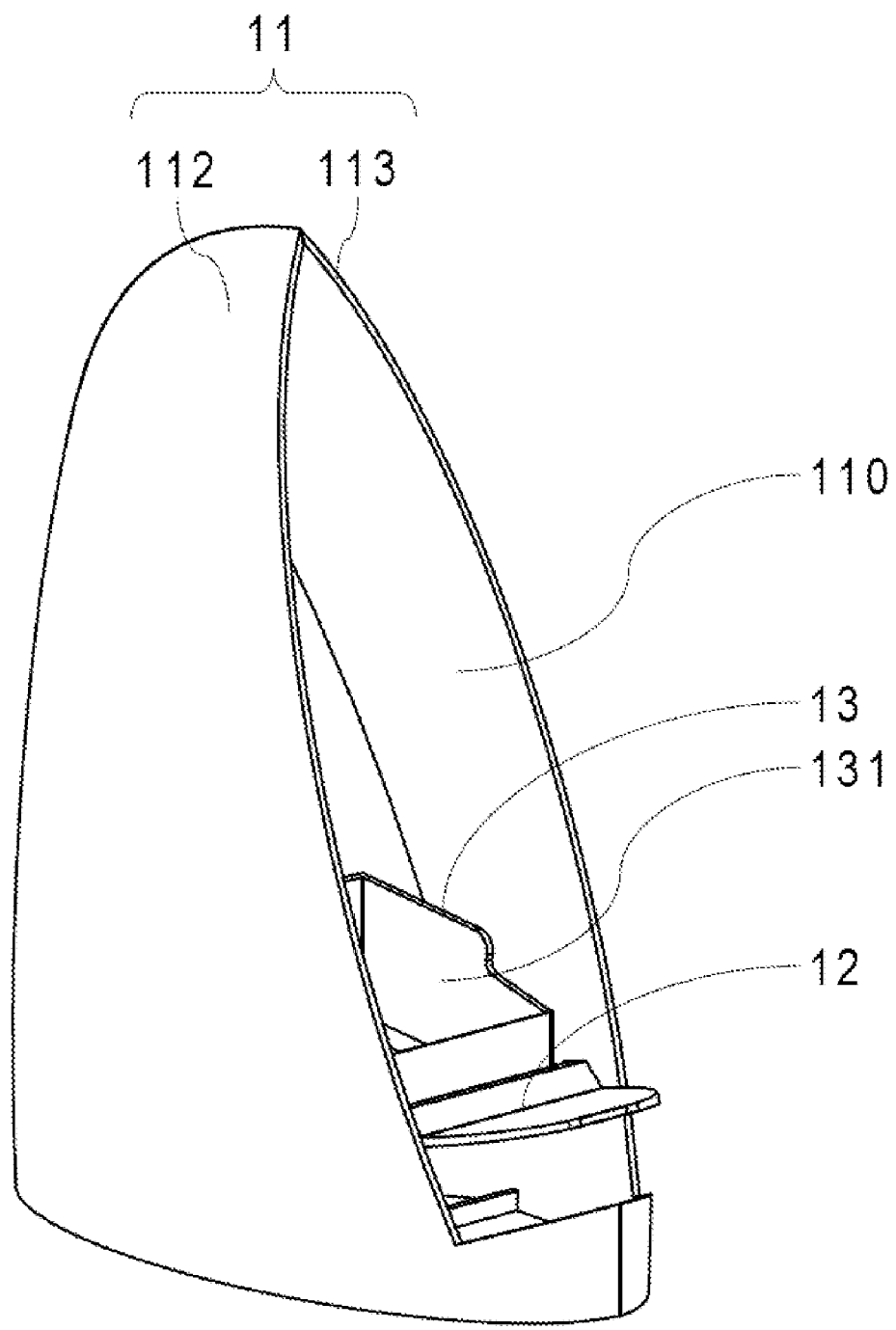
FIG. 1A is a plain view illustrating the ear thermometer cradle in a first embodiment of the present invention.
Figure 1B:
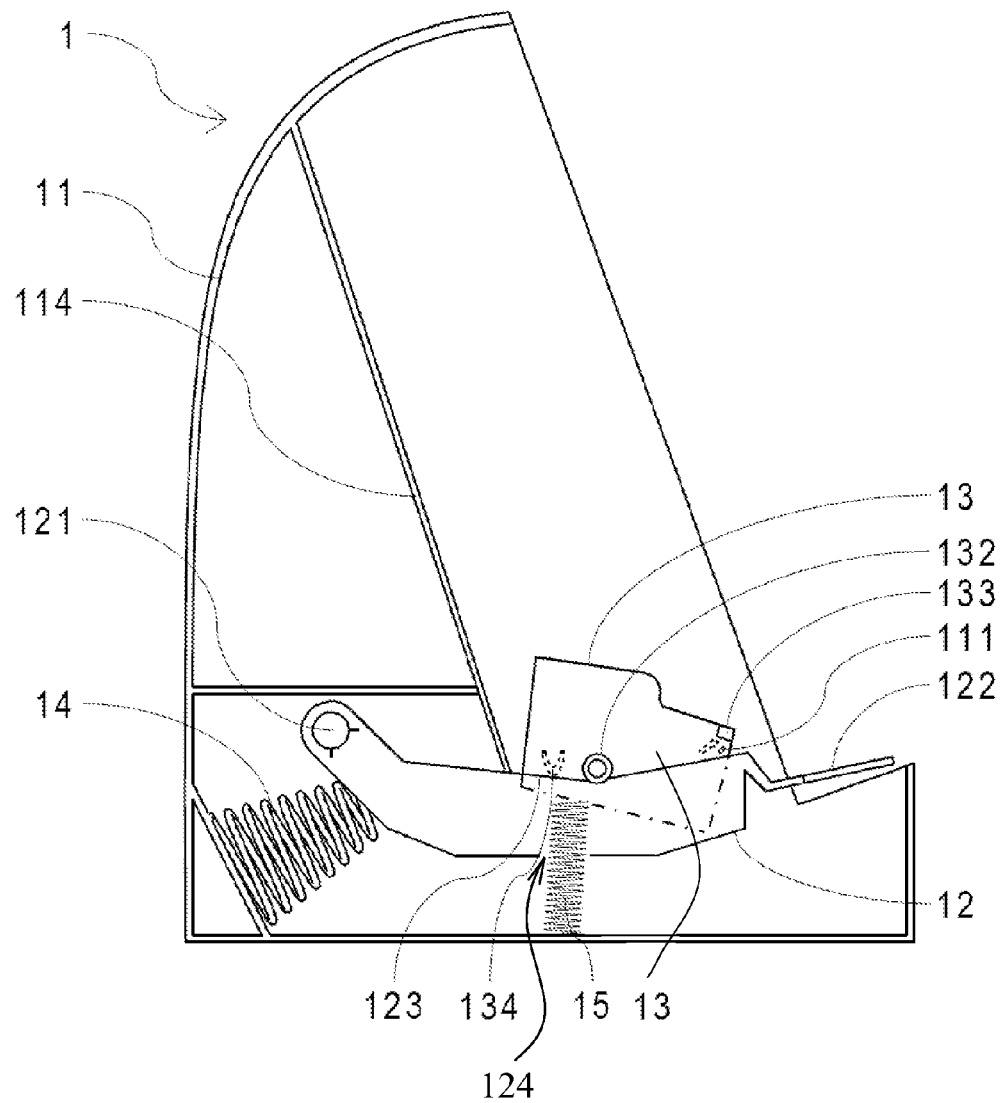
FIG. 1B is a sectional view illustrating the ear thermometer cradle in the first preferred embodiment of the present invention.

Please refer to FIG. 1A and FIG. 1B first. FIG. 1A is a plain view and FIG. 1B is sectional view illustrating an ear thermometer cradle in a first embodiment of the present invention. The ear thermometer cradle 1 includes a hollow housing 11, a swivel arm 12, a probe cover container seat 13, a first elastic member 14. The ear thermometer cradle 1 may also comprise a second elastic member 15. As shown in FIG. 1A, the hollow housing 11 is assembled by a first housing portion 112 and a second housing portion 113. Nevertheless, the hollow housing 11 can be an integral part made by injection molding.

The hollow housing 11 includes an opening 110 and a first blocking portion 111 disposed in the hollow housing 11. There is a first pivot 121 disposed at one end of the swivel arm 12 and the swivel arm 12 is pivotally connected to the hollow housing 11 by the first pivot 121. A bearing portion 122 is disposed on the other end of the swivel arm 12 and used to support the bottom of the ear thermometer (not shown). For disposing the ear thermometer conveniently, the bearing portion 122 is normally extended from the opening 110 of the hollow housing 11 when the ear thermometer (not shown) is not put in the ear thermometer cradle 1. When the ear thermometer (not shown) is put in the ear thermometer cradle 1, the bearing portion 122 will be pressed downwardly and hide into the opening 110 of the hollow housing 11. There is a second blocking portion 123 disposed between the first pivot 121 and the bearing portion 122. A first elastic element 14 is disposed between the swivel arm 12 and the hollow housing 11. The first elastic member 14 is deformed elastically when the ear thermometer (not shown) is not put in the thermometer cradle 1, and the elastic recovery strength of the first elastic member 14 will push the swivel arm 12 outwardly so that the bearing portion 122 will extends from the opening 110 of the hollow housing 11. The elastic member 14 is a component that can provide working strength of the swivel arm 12, and the elastic member 14 is preferred to be a compression spring.

In addition, the connective device 131 is disposed at the center of the probe cover container seat 13, and the second pivot 132 is disposed on two lateral sides of the probe cover container seat 13 to pivotally connect the probe cover container seat 13 with the hollow housing 11. The second elastic member 15 is disposed between the probe cover container seat 13 and the hollow housing 11. The second elastic member 15 is deformed elastically when the ear thermometer (not shown) is not put in the ear thermometer cradle 1. The elastic recovery strength of the second elastic member 15 will pull the probe cover container seat 13 downwardly. The probe cover container seat 13 further comprises a third blocking portion 133 and a forth blocking portion 134. The third blocking portion 133 engages with the first blocking portion 111 of the hollow housing 11, and the forth blocking portion 134 engages with the second blocking portion 123 of the swivel arm 12. The disposed position and configuration of the second elastic member 15 is to provide the working strength of the probe cover container seat 13 and is disposed between the probe cover container seat 13 and the hollow housing 11. Preferably, the second elastic member 15 is disposed between the bottom of the probe cover container seat 13 and the hollow housing 11. When the second elastic member 15 is disposed between the bottom of the probe cover container seat 13 and the hollow housing 11, the second elastic member 15 is preferable a tension spring, and the swivel arm 12 further includes a hole 124 for the second elastic member 15 passing through.

According to the above-mentioned configuration of the ear thermometer cradle 1, when the ear thermometer (not shown) is not put in the ear thermometer cradle 1, the first elastic member 14 is compressed so that the recovery strength of the first elastic member 14 will act on the swivel arm 12 and generate a torque on the swivel arm 12 in the counter clockwise direction in accordance with the first pivot 121. Because the second blocking portion 123 of the swivel arm engages with the forth blocking portion 134 of the probe cover container seat 13, the elastic recovery strength of the first elastic member 14 will be transferred to the probe cover container seat 13 through the swivel arm 12 and generate an engaging force in an upward direction on the forth blocking portion 134 of the probe cover container seat 13. Therefore, in accordance with the second pivot 132, a torque in the clockwise direction of the probe cover container seat 13 is generated. Moreover, the second elastic member 15 is in a tension deformation condition so as to exert a downward pulling force acting on the probe cover container seat 13 and a torque in counter clockwise direction acting on the probe cover container seat 13 in accordance with the second pivot 132. However, in this embodiment, the clockwise torque of the probe cover container seat 13 exerted by the second blocking portion 123 engaging with the forth blocking portion 134 will be larger than the counter-clockwise torque of the probe cover container seat 13 exerted by the second elastic member 15. Therefore, the probe cover container seat 13 tends to swivel counter-clockwise to make the third blocking portion 133 engage with the first blocking portion 111. However, the first blocking portion 111 will provide another supporting force in an upward direction acting on the third blocking portion 133 of the probe cover container seat 13 and generate a counter-clockwise torque acting on the probe cover container 13. Therefore, the summation of the torques acting on the probe cover container 13, which are respectively generated by the second blocking 123 of the swivel arm 12, the second elastic member 15 and the first blocking portion 111 of the hollow housing 11, equals to zero so that the probe cover container seat 13 is in a condition of static equilibrium.

The connective device 131 of the probe cover container seat 13 is used to connect the probe cover container (not shown here) disposed in the probe cover container seat 13. The design of the connective device 131 is accordance with the probe cover container and would be a holder with a protruding configuration to hold the probe cover (not shown here) in the probe cover container. Or the connective device 131 can be a container with a concave configuration for accommodating the probe cover container.

In addition to the first preferred embodiment, a second preferred embodiment of the ear thermometer assembly is also proposed according to concept of the present invention.

Figure 2A:
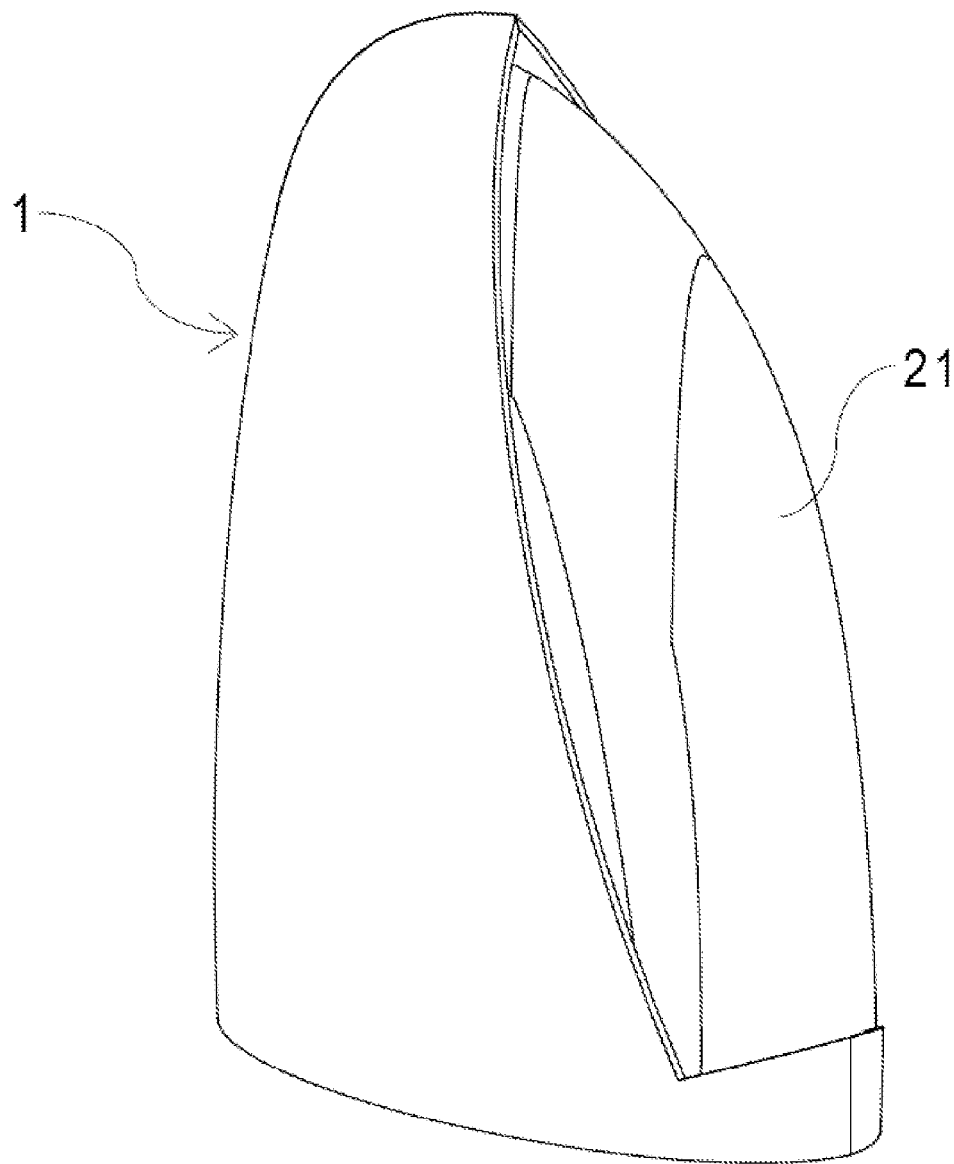
FIG. 2A is a view illustrating the ear thermometer cradle assembly in a second embodiment of the present invention.

FIG. 2A is a plain view of the second preferred embodiment which is an ear thermometer assembly. The ear thermometer cradle assembly 2 includes an ear thermometer 21, an ear thermometer cradle 1, and a probe cover container 22 (shown in FIG. 2B).

Figure 2B:
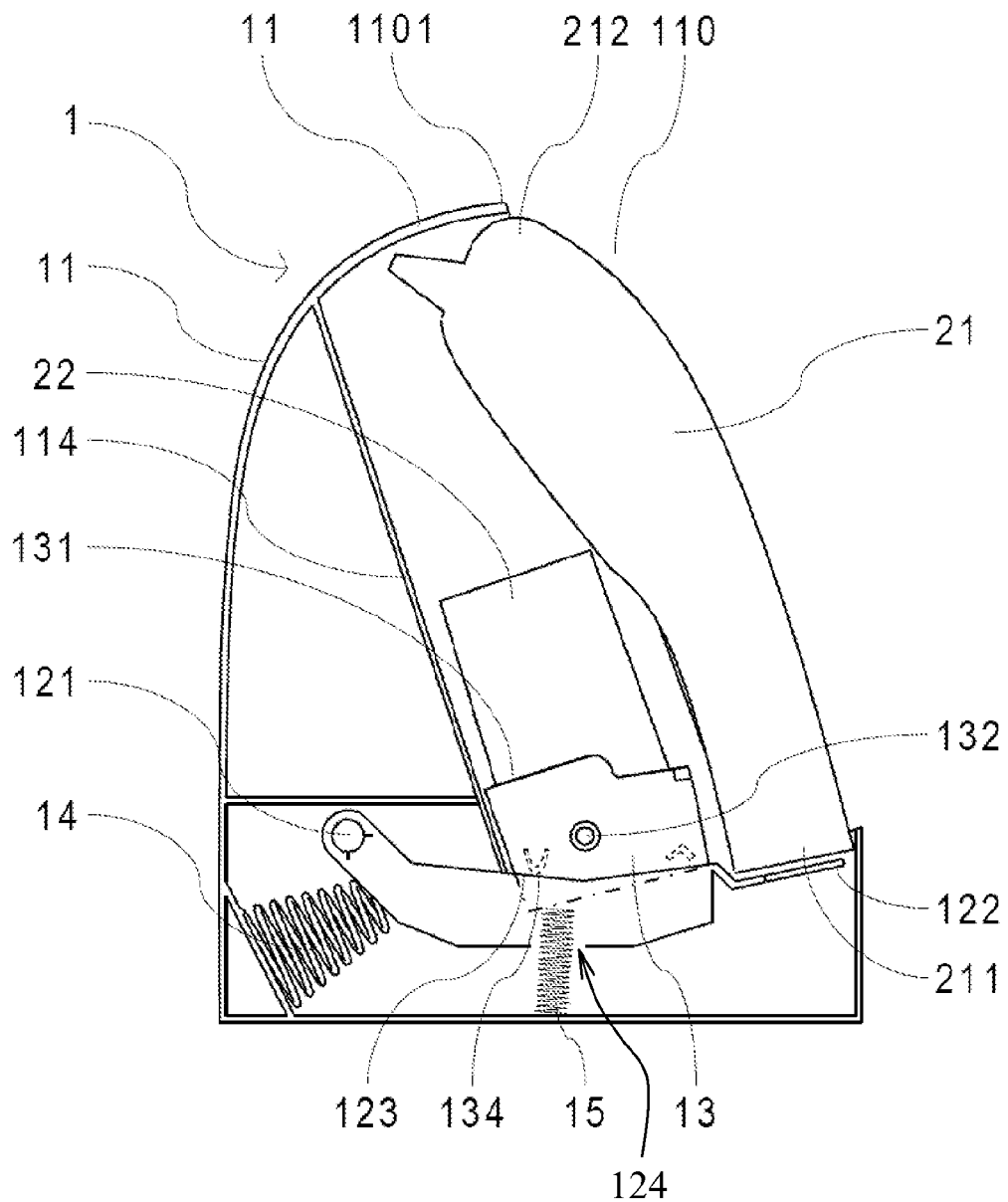
FIG. 2B is a sectional view illustrating the ear thermometer cradle assembly in the second preferred embodiment of the present invention.

Please refer to FIG. 2B. FIG. 2B is a sectional view of the ear thermometer cradle 2. The bearing portion 122 of the swivel arm 12 is used to bear the bottom 211 of the ear thermometer 21. The probe cover container 22 is disposed in the connective device 131 of the probe cover container seat 13. In addition, the ear thermometer cradle 1 in the present embodiment includes substantially the same components as shown in the first embodiment. Therefore, the detail description of the ear thermometer cradle 1 is omitted herein.

When the ear thermometer 21 is not put in the ear thermometer cradle 1 of the ear thermometer assembly 2, the configuration of the components of the ear thermometer cradle 1 and the exerting force thereof are the same as the first embodiment. The following description will describe the relative motion occurred between components of the ear thermometer cradle 1 after the ear thermometer 21 is stored or put in the ear thermometer cradle 1.

The ear thermometer 21 is put in the thermometer cradle 1 via the opening 110 of the thermometer cradle 1. The bottom 211 of the ear thermometer 21 presses the bearing portion 122 of the swivel arm 12 downwardly so that the swivel arm 12 will rotate clockwise in accordance with the first pivot 121 and the first elastic member 14 will be pressed further. Thus, the second blocking portion 123 move downward and tends to disengage from the forth blocking portion 134 of the probe cover container seat 13 and won't be able to exert the upward supporting force acting on the probe cover container seat 13. In the mean time, the elastic recovery strength of the second elastic member 15 resulted from its tension deformation drags the probe cover container seat 13 to rotate counter-clockwise in accordance with the second pivot 132 so that the probe cover container 22 rotate along with the probe cover container seat 13 into the hollow housing 11 until the probe cover container seat 13 is stopped by the bearing slope 114 of the hollow housing 11.

After the ear thermometer 21 is put into the ear thermometer cradle 1, the bottom 211 of the ear thermometer 21 will be born the elastic recovery strength generated by the first elastic member 14 from the bearing portion 122. At this moment, the top portion 212 of the ear thermometer 21 in the opening 110 engages with the upper edge 1101 of the opening 110. The ear thermometer 21 is thus fixed in the opening 110 in accordance with the elastic recovery strength of the first elastic member 14.

When the ear thermometer 21 is released from the ear thermometer cradle 1, the ear thermometer 21 is first pressed downward so that the swivel arm 12 rotates clockwise. And the first elastic member 14 is compressed further. At this moment, the top portion 212 of the ear thermometer 21 and the upper edge 1101 of the opening 110 disengages from each other, and the ear thermometer 21 is able to slant backward so as to be taken out from the opening 110.

Figure 2C:
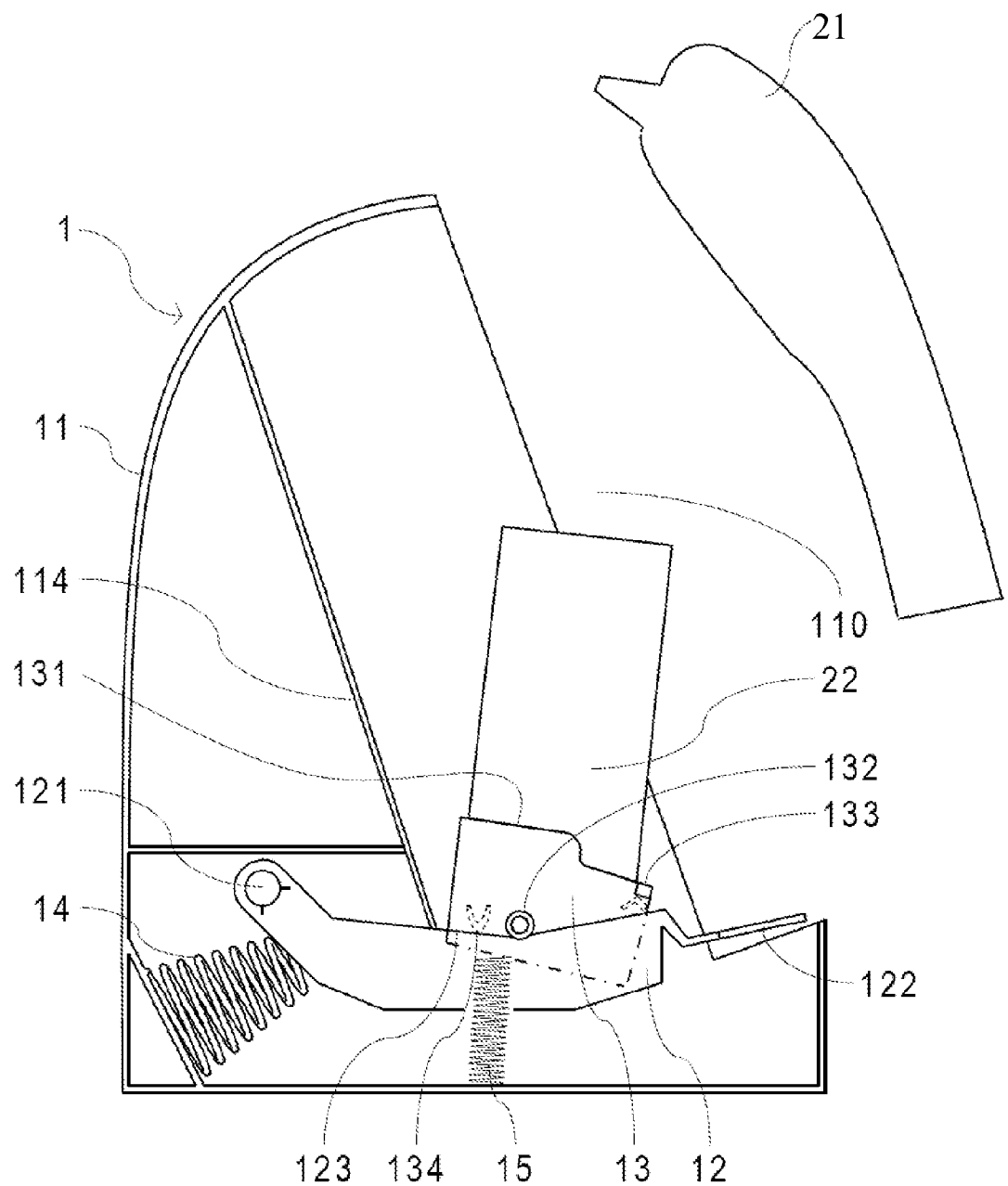
FIG. 2C is another view illustrating that the ear thermometer cradle assembly in the second preferred embodiment of the present invention.

Now please refer to FIG. 2C. FIG. 2C is another sectional view of the second preferred embodiment in the present invention. When the ear thermometer 21 is removed from the ear thermometer cradle 1, the swivel arm 12 rotates counter clockwise in accordance with the first pivot 121 due to the elastic recovery strength generated by the compression deformation of the first elastic member 14. At this moment, the second blocking portion 123 of the swivel arm 12 engages to the forth blocking portion 134 of the probe cover container seat 13 and will provide an upward force acting on the probe cover container seat 13. Thus the probe cover container seat 13 and the probe cover container 22 rotate clockwise in accordance with the second pivot 132. The probe cover container 22 is thus extended from the opening 110. The user can put the probe cover (not shown here) on the ear thermometer 21 without touching the probe cover (not shown here) to avoid the biological contamination of the probe cover (not shown here).

Because the operations of putting the ear thermometer 21 in the ear thermometer cradle 1, taking the ear thermometer 21 from the ear thermometer cradle 1, and accessing the probe cover container 22 stored in the probe cover container seat 13, are based on relative motions of the swivel arm 12, the first elastic member 14, the probe cover container seat 13, and the second elastic member 15. The user can take out and put back the ear thermometer 21 by one hand, and the probe cover container 22 will rotates and extends from the opening 110 of the ear thermometer cradle 1 when taking out the ear thermometer 21 from the ear thermometer cradle 1. Accordingly, the directions of the forces exerted from the operations carried out by users are generally downward. Therefore, when the ear thermometer cradle of the present invention is put on a solid plane, the user can take out and put back the ear thermometer 21 by one hand. Such configurations of the present invention are distinct from those of the conventional ear thermometer that needs two-handed operations.

The preferred embodiments of the present invention are herein provided for illustrative purposes only and not intended to limit the scope of the present invention in any way. Moreover, as the contents disclosed herein should be readily understood and can be implemented by a person skilled in the art, all equivalent changes or modifications which do not depart from the spirit of the present invention should be encompassed by the appended claims

What is claimed is:

1. An ear thermometer cradle, comprising:
    a hollow housing including an opening and a first blocking portion disposed therein;
    a swivel arm including a first pivot on one end thereof for pivotally connected with said hollow housing, a bearing portion on the other end thereof, and a second blocking portion disposed between said first pivot and said bearing portion;
    a probe cover container seat including a connective device therein, a second pivot on two lateral sides thereof for pivotally connected with said hollow housing, a third blocking portion engaging with said first blocking portion, and a forth blocking portion engaging with said second blocking portion;
    a first elastic member disposed between said swivel arm and said hollow housing.

2. The ear thermometer cradle of claim 1, wherein the ear thermometer cradle comprises a second elastic member disposed between said probe cover container seat and said hollow housing.

3. The ear thermometer cradle of claim 1, wherein said second elastic element is disposed between the bottom of said probe cover container and said hollow housing.

4. The ear thermometer cradle of claim 3, wherein said second elastic element is a tension spring.

5. The ear thermometer cradle of claim 4, wherein said swivel arm further includes a hole and said second elastic element is passed through said hole.

6. The ear thermometer cradle of claim 1, wherein said first elastic element is a compression spring.

7. The ear thermometer cradle of claim 1, wherein said hollow housing further includes and is assembled by a first housing portion and a second housing portion.

8. The ear thermometer cradle of claim 1, wherein said connective device is a container with a concave configuration.

9. The ear thermometer cradle of claim 1, wherein said connective device is a holder with a protruding configuration.

10. The ear thermometer cradle of claim 1, wherein said bearing portion is extended from said opening of said hollow housing.

11. An ear thermometer cradle assembly comprising an ear thermometer, a probe cover container and an ear thermometer cradle, and said thermometer cradle comprises:
    a hollow housing including an opening and a first blocking portion disposed therein;
    a swivel arm including a first pivot on one end thereof for pivotally connected with said hollow housing, a bearing portion on the other end thereof, and a second blocking portion disposed between said first pivot and said bearing portion, wherein said bearing portion is for supporting the bottom of the ear thermometer;

a probe cover container seat including a connective device in the center thereof, a second pivot on two lateral sides for pivotally connected with said hollow housing, a third blocking portion for blocking said first blocking portion, and a forth blocking portion for blocking said second blocking portion, wherein said probe cover container seat holds said probe cover container;

a first elastic member disposed between said swivel arm and said hollow housing.

12. The ear thermometer cradle of claim 11, wherein the ear thermometer cradle comprises a second elastic member disposed between said probe cover container seat and said hollow housing.

13. The ear thermometer cradle assembly of claim 11, wherein said second elastic element is disposed between the bottom of said probe cover container and said hollow housing.

14. The ear thermometer cradle assembly of claim 13, wherein said second elastic element is a tension spring.

15. The ear thermometer cradle assembly of claim 14, wherein said swivel arm further includes a hole, and said second elastic element is passed through said hole.

16. The ear thermometer cradle assembly of claim 11, wherein said first elastic element is a compression spring.

17. The ear thermometer cradle assembly of claim 11, wherein said hollow housing further includes and is assembled by a first housing portion and a second housing portion.

18. The ear thermometer cradle assembly of claim 11, wherein said connective device is a container with a concave configuration.

19. The ear thermometer cradle assembly of claim 11, wherein said connective device is a holder with a protruding configuration.

20. The ear thermometer cradle assembly of claim 11, wherein said hearing portion is extended from said opening of said hollow housing.

* * * * *